US011524125B2

(12) United States Patent (10) Patent No.: US 11,524,125 B2
Nagasawa (45) Date of Patent: Dec. 13, 2022

(54) PUNCTURE NEEDLE

(71) Applicant: TERUMO KABUSHIKI KAISHA, Tokyo (JP)

(72) Inventor: Masahiko Nagasawa, Nakakoma-gun (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/918,216

(22) Filed: Jul. 1, 2020

(65) Prior Publication Data

US 2020/0330700 A1 Oct. 22, 2020

(30) Foreign Application Priority Data

Feb. 14, 2018 (JP) .............................. JP2018-024326

(51) Int. Cl.
*A61M 5/32* (2006.01)
(52) U.S. Cl.
CPC ................................ *A61M 5/3286* (2013.01)
(58) Field of Classification Search
CPC ............................. A61M 5/3286; A61M 5/158
See application file for complete search history.

(56) References Cited

U.S. PATENT DOCUMENTS 2,716,983 A   9/1955  Windischman et al.
3,308,822 A * 3/1967  De Luca ............. A61M 5/3286
                                                         604/274
5,752,942 A * 5/1998  Doyle ..................... B24B 19/16
                                                         604/274
6,517,523 B1 * 2/2003  Kaneko ............... A61M 5/3286
                                                         604/272

(Continued)

FOREIGN PATENT DOCUMENTS

CN       1646182 A       7/2005
CN     203154450 U       8/2013

(Continued)

OTHER PUBLICATIONS

International Searching Authority, "International Search Report," issued in connection with International Patent Application No. PCT/JP2018/046395, dated Mar. 19, 2019.

(Continued)

*Primary Examiner* — James D Ponton
*Assistant Examiner* — Neeraja Gollamudi
(74) *Attorney, Agent, or Firm* — Foley & Lardner LLP

(57) ABSTRACT

A puncture needle includes: a rod-shaped main body; and a blade surface located at a distal end portion of the main body, which includes: first, second, and third blade surface portions. The first blade surface portion and the second blade surface portion form a blade edge at a ridge line where the first blade surface portion and the second blade surface portion meet, wherein a needle tip is located at a distal end of the blade edge. The third blade surface portion is contiguous with a proximal side of at least the first blade surface portion, and the third blade surface portion is a single flat surface that is inclined with respect to a central axis of the main body. In a side view of the main body, a line extending along the third blade surface portion intersects with the first blade surface portion.

10 Claims, 14 Drawing Sheets

(56) References Cited

U.S. PATENT DOCUMENTS

| | | | |
|---|---|---|---|
| 7,435,239 B2* | 10/2008 | Yatabe | A61M 5/3286 604/272 |
| 2013/0218102 A1* | 8/2013 | Iwase | A61M 5/3286 451/28 |
| 2015/0196747 A1* | 7/2015 | Alvarez | A61M 5/3286 606/131 |
| 2015/0209180 A1* | 7/2015 | Prausnitz | A61M 37/0015 604/521 |
| 2016/0206832 A1* | 7/2016 | Kurose | A61F 9/00736 |
| 2016/0317757 A1* | 11/2016 | Ooyauchi | B21G 1/08 |
| 2016/0338734 A1* | 11/2016 | Shah | A61M 5/3286 |
| 2017/0252520 A1* | 9/2017 | Higaki | A61B 17/3417 |
| 2017/0274153 A1* | 9/2017 | Ueda | A61B 5/150396 |

FOREIGN PATENT DOCUMENTS

| | | |
|---|---|---|
| CN | 105939740 A | 9/2016 |
| DE | 10207770 A1 | 9/2003 |
| JP | H09-149936 A | 6/1997 |
| JP | H10-57490 A | 3/1998 |
| JP | 2000-262615 A | 9/2000 |
| WO | WO-2017/017935 A1 | 2/2017 |

OTHER PUBLICATIONS

International Searching Authority, "Written Opinion," issued in connection with International Patent Application No. PCT/JP2018/046395, dated Mar. 19, 2019.

Office Action dated Nov. 23, 2021 in a corresponding Chinese Patent Application No. 201880089184.X, (12 pages).

* cited by examiner

PUNCTURE NEEDLE

CROSS-REFERENCE TO RELATED APPLICATIONS

This is a bypass continuation of PCT Application No. PCT/JP2018/046395, filed on Dec. 17, 2018, which claims priority to Japanese Application No. 2018-024326, filed on Feb. 14, 2018. The contents of these applications are hereby incorporated by reference in their entireties.

BACKGROUND

The present disclosure relates to a puncture needle.

As a medical puncture needle such as a blood sampling needle or an indwelling needle for infusion, a conventionally known puncture needle has a distal end portion provided with a plurality of blade surfaces having different angles with respect to the longitudinal direction of the puncture needle in order to reduce pain when the puncture needle is inserted into a human body.

JP 2000-262615 A discloses an injection needle as the puncture needle described above. The injection needle disclosed in JP 2000-262615 A includes a tapered tip portion formed by cutting a tip portion of a cylindrical main body obliquely from one side thereof, the tapered tip portion of the needle including: a first inclined surface connected to an outer periphery of the cylindrical main body and formed at a predetermined angle with respect to an axial direction (longitudinal direction) of the main body; a second inclined surface connected to the first inclined surface and formed at a larger angle than the predetermined angle of the first inclined surface with respect to the axial direction of the main body; and a third inclined surface connected to the second inclined surface, connected to a tip of a blade, and formed at a larger angle than the angle of the second inclined surface with respect to the axial direction of the main body.

JP 10-57490 A also discloses a hypodermic injection needle as a puncture needle. The hypodermic injection needle disclosed in JP 10-57490 A has a multi-beveled tip, the multi-beveled tip having a primary bevel, a pair of intermediate bevels, and a pair of tip bevels.

SUMMARY

When an injection needle has a distal end portion provided with a blade surface formed by connecting a plurality of surfaces having different angles with respect to the longitudinal direction, like the injection needles disclosed in JP 2000-262615 A and JP 10-57490 A, puncture resistance due to a ridge line (junction) formed on the boundary between surfaces can be reduced, whereby pain during puncture of the injection needle into a human body can be alleviated.

Meanwhile, regarding a puncture needle that is inserted into a vessel such as a blood vessel, it is common to use a puncture needle having a shorter length of a blade surface (hereinafter referred to as a "blade surface length") in a central axis direction in order to allow the entire blade surface to be easily inserted into the vessel. In such a puncture needle having a shorter blade surface length, even if the blade surface is constituted by multiple surfaces having different angles with respect to the central axis direction, the angle of the blade tip of the blade surface (hereinafter referred to as a "blade tip angle") in a side view cannot be reduced, and the blade tip angle tends to be relatively large. Therefore, such a puncture needle has a problem that the puncture resistance of the blade tip is increased, which makes it difficult to alleviate pain during puncture of the blade tip. In addition, when the puncture resistance of the blade tip is large, the blade tip cannot smoothly pierce a vessel wall such as a blood vessel wall during puncture into the vessel, and the vessel may avoid by being pushed by the blade tip.

In view of the above, an object of certain embodiments of the present disclosure is to provide a puncture needle having a blade surface shape capable of reducing a blade tip angle regardless of a blade surface length.

A puncture needle according to one embodiment of the present invention is a puncture needle for medical use provided with a blade surface formed on a distal end portion of a main body that is rod-shaped, in which the blade surface includes: a first blade surface portion and a second blade surface portion that form a blade edge having a needle tip as one end by a ridge line where the first blade surface portion and the second blade surface portion meet; and a third blade surface portion that is contiguous with at least one blade surface portion from among the first blade surface portion and the second blade surface portion on a proximal side of the main body and that is constituted by a single flat surface inclined with respect to a central axis of the main body, and in a side view of the main body in which the single flat surface appears straight, a line extending along the third blade surface portion intersects with one blade surface portion that is visible in the side view from among the at least one blade surface portion.

According to one aspect of the present invention, the line extending along the third blade surface portion intersects with the one blade surface portion at a position not on the blade edge in the side view.

According to one aspect of the present invention, a distal end of the third blade surface portion reaches the central axis in the side view, or the third blade surface portion intersects with the central axis in the side view.

According to one aspect of the present invention, the central axis overlaps with the one blade surface portion in the side view.

According to one aspect of the present invention, the first blade surface portion and the second blade surface portion extend to a proximal side beyond a midpoint of a blade surface region in a central axis direction of the main body.

A puncture needle according to a second embodiment of the present invention is a puncture needle for medical use provided with a blade surface formed on a distal end portion of a main body that is rod-shaped, wherein the blade surface includes: a first blade surface portion and a second blade surface portion that form a blade edge having a needle tip as one end by a ridge line where the first blade surface portion and the second blade surface portion meet; and a third blade surface portion that is contiguous with proximal sides of the first blade surface portion and the second blade surface portion, and the third blade surface portion has a concave shape in a side view of the main body.

According to one aspect of the present invention, the third blade surface portion is constituted by a concave curved surface.

According to one aspect of the present invention, the third blade surface portion is constituted by a plurality of flat surfaces.

According to one aspect of the present invention, a distal end of the third blade surface portion reaches the central axis of the main body in the side view, or the third blade surface portion intersects with the central axis of the main body in the side view.

According to one aspect of the present invention, in the side view, the central axis of the main body overlaps with one blade surface portion that is visible in the side view from among the first blade surface portion and the second blade surface portion.

According to one aspect of the present invention, the first blade surface portion and the second blade surface portion extend to a proximal side beyond a midpoint of a blade surface region in a central axis direction of the main body.

The present disclosure can provide a puncture needle having a blade surface shape capable of reducing a blade tip angle, regardless of a blade surface length.

DETAILED DESCRIPTION

Figure 1A:
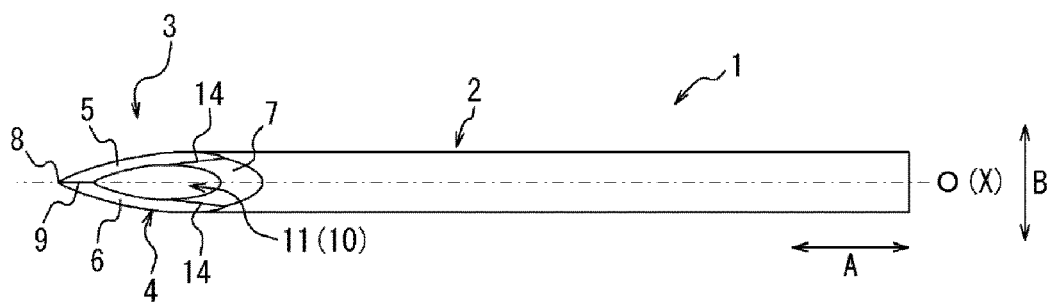
FIGS. 1A through 1D are a front view, a side view, a rear view, and a perspective view of a main body of a puncture needle as one embodiment, respectively.

Hereinafter, an embodiment of a puncture needle according to the present disclosure will be described with reference to FIGS. 1 to 11. In the drawings, same members and parts are denoted by the same reference numerals.

First Embodiment

Figure 1B:
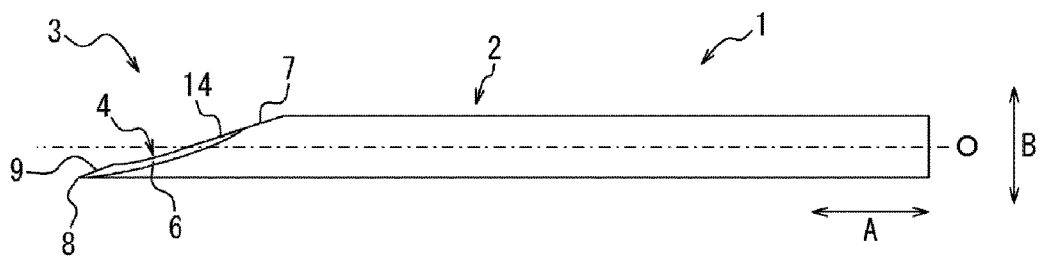
Figure 1C:
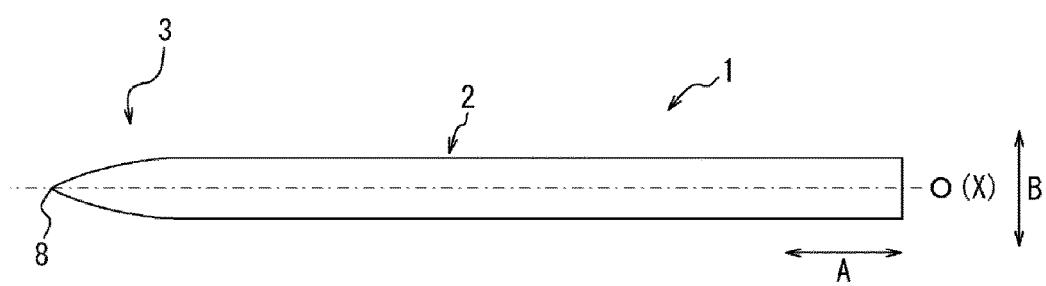
Figure 1D:
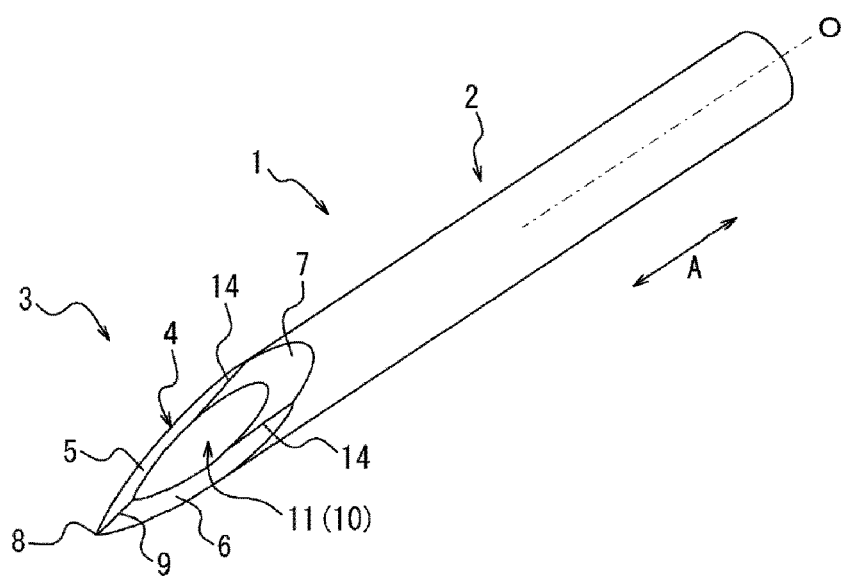
Figure 2A:
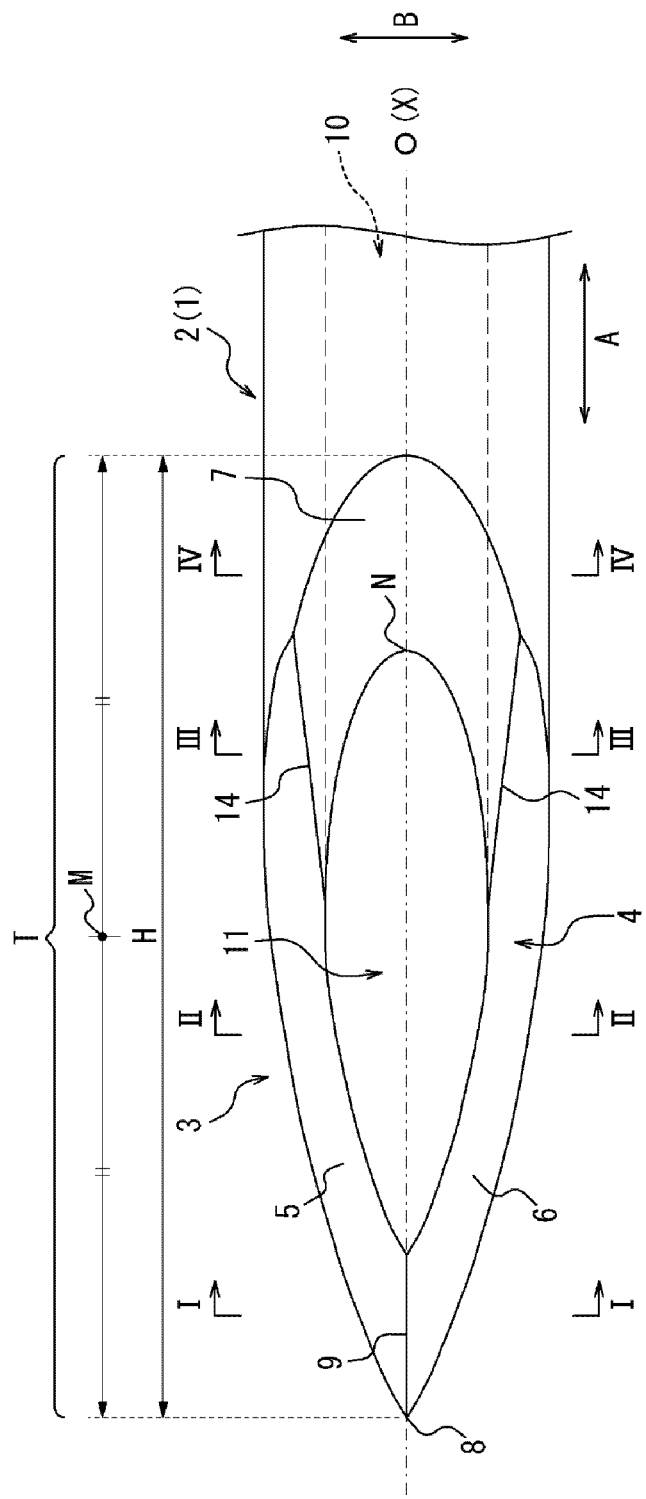
FIGS. 2A and 2B are enlarged views showing the vicinity of a distal end portion of the main body of the puncture needle shown in FIGS. 1A and 1B, respectively.
Figure 2B:
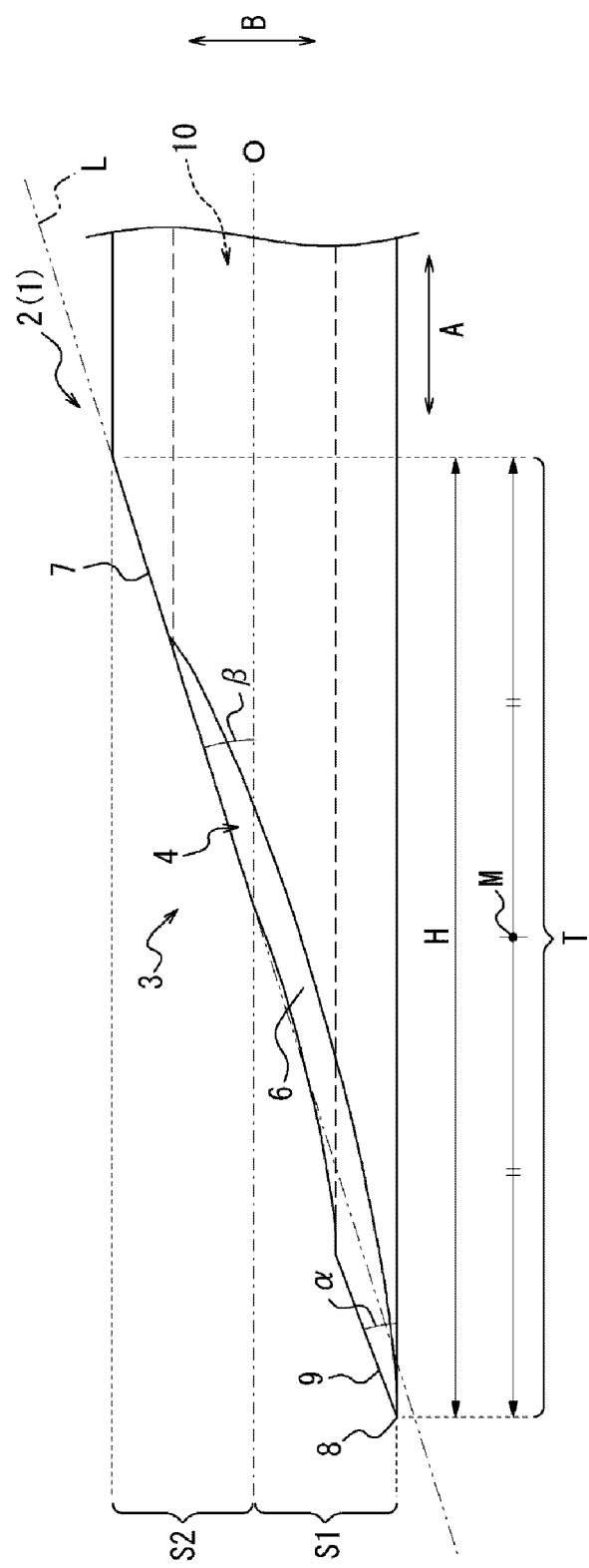

FIG. 1 is a view showing a main body 2 of a puncture needle 1 as one embodiment. Specifically, FIG. 1A is a front view of the main body 2 of the puncture needle 1, FIG. 1B is a side view of the main body 2 of the puncture needle 1, and FIG. 1C is a rear view of the main body 2 of the puncture needle 1. FIG. 1D is a perspective view of the main body 2 of the puncture needle 1. Further, FIG. 2A is an enlarged front view of a part of the main body 2 of the puncture needle 1 shown in FIG. 1A. FIG. 2B is an enlarged side view of a part of the main body 2 of the puncture needle 1 shown in FIG. 1B.

As shown in FIGS. 1A to 1D, 2A, and 2B, the puncture needle 1 has the rod-shaped main body 2, and a blade surface 4 is formed at a distal end portion 3 of the main body 2. The main body 2 in the present embodiment is a tubular body, and defines a hollow portion 10 extending in an axial direction (hereinafter referred to as a "central axis direction A") parallel to a central axis O of the main body 2.

More specifically, the main body 2 in the present embodiment is a tubular body in which a cross section perpendicular to the central axis direction A has a substantially circular outer shape.

As shown in FIGS. 1A to 1D, 2A and 2B, the blade surface 4 is constituted by a plurality of blade surface portions. The blade surface 4 in the present embodiment includes a first blade surface portion 5 constituted by a single flat surface, a second blade surface portion 6 constituted by a single flat surface, and a third blade surface portion 7 constituted by a single flat surface.

The first blade surface portion 5 and the second blade surface portion 6 of the blade surface 4 are formed on the distal side of the blade surface 4. Further, the first blade surface portion 5 and the second blade surface portion 6 form a blade edge 9 having the needle tip 8 as one end by a ridge line where they meet. The "needle tip" means the tip of the puncture needle 1 in the central axis direction A, that is, the tip of the main body 2, and also means a blade tip that is the tip of the blade surface 4. Therefore, in the following description, the "distal side" means the needle tip side in the central axis direction A, and the "proximal side" means the side opposite to the needle tip side in the central axis direction A.

A proximal side of the first blade surface portion 5 is contiguous with a distal side of the third blade surface portion 7. Further, a proximal side of the second blade surface portion 6 is contiguous with a distal side of the third blade surface portion 7. That is, the distal side of the third blade surface portion 7 in the present embodiment is contiguous with the proximals sides of both the first blade surface portion 5 and the second blade surface portion 6.

More specifically, the third blade surface portion 7 is constituted by a single flat surface that is inclined with respect to the central axis O of the main body 2. Further, the third blade surface portion 7 in the present embodiment forms a proximal end of the blade surface 4. In other words, a proximal side of the third blade surface portion 7 in the present embodiment is contiguous with the cylindrical outer peripheral surface of the main body 2. Therefore, in the present embodiment, a distal side of the third blade surface portion 7 is contiguous with the proximal sides of the first blade surface portion 5 and the second blade surface portion 6, and a proximal side of the third blade surface portion 7 is contiguous with the distal side of the cylindrical outer peripheral surface of the main body 2.

As described above, the blade surface 4 in the present embodiment is formed by continuously connecting flat blade surface portions.

The inner edge of the blade surface 4 in the present embodiment is constituted by the inner edge of the first blade surface portion 5, the inner edge of the second blade surface portion 6, and the inner edge of the third blade surface portion 7. The inner edge of the blade surface 4 defines a distal-end opening 11, which is one end of the hollow portion 10 of the main body 2 on the distal side of the main body 2.

The outer edge of the blade surface 4 in the present embodiment is defined by the outer edge of the first blade surface portion 5, the outer edge of the second blade surface portion 6, and the outer edge of the third blade surface portion 7. The outer edge of the blade surface 4 defines a blade surface region T where the blade surface 4 is formed. Therefore, the maximum length of the outer edge of the blade surface 4 in the central axis direction A is a length H of the blade surface in the central axis direction A (hereinafter, referred to as "blade surface length H").

Here, in a side view of the main body 2 in which one flat surface constituting the third blade surface portion 7 appears straight (see FIGS. 1B and 2B), a line L extending along the third blade surface portion 7 intersects with a blade surface portion, which is visible in the side view, out of the first blade surface portion 5 and the second blade surface portion 6. In the side view shown in FIGS. 1B and 2B, the second blade surface portion 6 corresponds to the above-mentioned blade surface portion that is visible out of the first blade surface portion 5 and the second blade surface portion 6. Therefore, the line L extending along the third blade surface portion 7 intersects with the second blade surface portion 6 in the side view shown in FIGS. 1B and 2B. Hereinafter, "the side view of the main body 2 in which one flat surface constituting the third blade surface portion 7 appears straight" is simply referred to as a "side view of the main body 2".

Due to the configuration in which, in the side view of the main body 2 (see FIGS. 1B and 2B), the line L extending along the third blade surface portion 7 intersects with the blade surface portion, which is visible in the side view, out of the first blade surface portion 5 and the second blade surface portion 6 as described above, the puncture needle 1 having a smaller blade tip angle α can be easily achieved, compared with a configuration in which, in the side view, the line extending along the third blade surface portion 7 does not intersect with the blade surface portion, which is visible in the side view, out of the first blade surface portion 5 and the second blade surface portion 6. The "blade tip angle α" herein means an angle between the blade edge 9 and the back surface of the blade edge 9 at the needle tip 8 in the side view (see FIGS. 1B and 2B) of the main body 2. As shown in FIGS. 1B and 2B, the needle tip 8 is located on one end in a direction B perpendicular to the central axis direction A in the side view of the main body 2 in the present embodiment.

Figure 11:
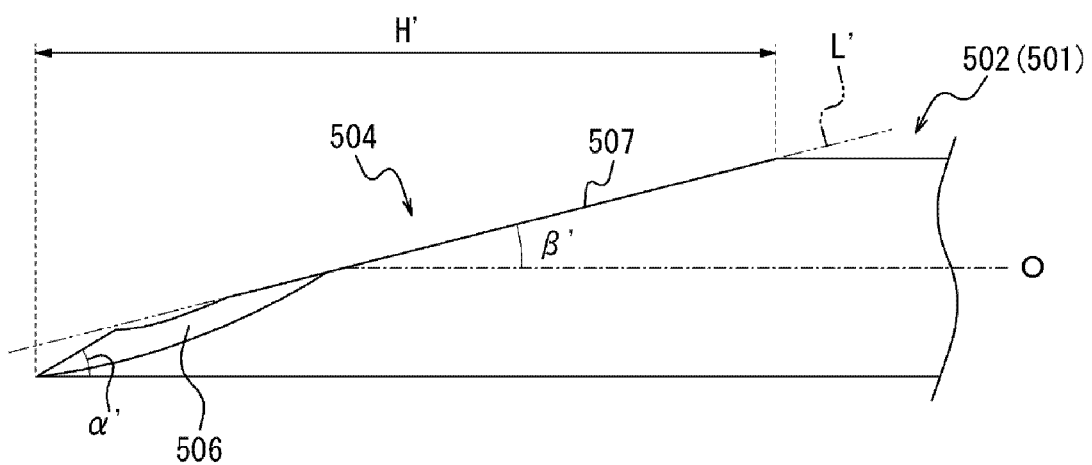
FIG. 11 is a side view of a main body of an existing puncture needle.

FIG. 11 is a side view of a main body 502 of an existing puncture needle 501 as viewed from side. The main body 502 of the existing puncture needle 501 shown in FIG. 11 has a blade surface 504 including a first blade surface portion (not shown) constituted by a single flat surface, a second blade surface portion 506 constituted by a single flat surface, and a third blade surface portion 507 constituted by a single flat surface. In the existing puncture needle 501 described above, a line L' extending along the third blade surface portion 507 does not intersect with the second blade surface portion 506 in the side view shown in FIG. 11. In the configuration described above, a blade tip angle α' is larger than an inclination angle V of the third blade surface portion 507 formed by the line L' extending along the third blade surface portion 507 and the central axis O.

Therefore, in the existing puncture needle 501, when the acute inclination angle V of the third blade surface portion 507 with respect to the central axis O is increased in order to reduce the blade surface length H, the blade tip angle α' also increases accordingly. That is, in the existing puncture needle 501, it is difficult to reduce both the blade surface length H' and the blade tip angle α'.

On the other hand, in the puncture needle 1, in the side view of the main body 2 (see FIGS. 1B and 2B), the line L extending along the third blade surface portion 7 intersects with the blade surface portion, which is visible in the side view, out of the first blade surface portion 5 and the second blade surface portion 6. With the configuration described above, the blade tip angle α can be smaller than the acute inclination angle β of the third blade surface portion 7 formed by the line L extending along the third blade surface portion 7 and the central axis O. Therefore, the puncture needle 1 can be configured such that, even when the inclination angle β of the third blade surface portion 7 with respect to the central axis O is increased in order to reduce the blade surface length H, the blade tip angle α does not increase accordingly. That is, the puncture needle 1 can be easily configured such that both the blade surface length H and the blade tip angle α are reduced.

In the puncture needle 1 in the present embodiment, a relation similar to the abovementioned relation is also established for the side (hereinafter referred to as the "opposite side") opposite to the side shown in FIGS. 1B and 2B. Specifically, in a side view seen from the opposite side, the line L extending along the third blade surface portion 7 intersects with a blade surface portion, which is visible in the side view, out of the first blade surface portion 5 and the second blade surface portion 6. In the side view seen from the opposite side, the first blade surface portion 5 corresponds to the blade surface portion that is visible out of the first blade surface portion 5 and the second blade surface portion 6. Therefore, the line L extending along the third blade surface portion 7 intersects with the first blade surface portion 5 in the side view seen from the opposite side.

The third blade surface portion 7 in the present embodiment is constituted by a flat surface contiguous with proximal sides of both the first blade surface portion 5 and the second blade surface portion 6. However, it is not limited to have the above configuration. The third blade surface portion may be constituted by a flat surface contiguous with the proximal side of either the first blade surface portion 5 or the second blade surface portion 6. Further, each of the first blade surface portion 5 and the second blade surface portion 6 may be contiguous with different flat surfaces constituting the third blade surface portion.

As described above, it is sufficient that the third blade surface portion is contiguous with the proximal side of at least one blade surface portion out of the first blade surface portion and the second blade surface portion. Further, it is sufficient that, in the side view of the main body in which one flat surface constituting the third blade surface portion appears straight, the line extending along the third blade surface portion intersects with one blade surface portion, which is visible in the side view, from among the at least one blade surface portion contiguous with the third blade surface portion.

However, if the third blade surface portion 7 is used that is contiguous with the proximal sides of both the first blade surface portion 5 and the second blade surface portion 6 and that is constituted by a single flat surface as in the present embodiment described above, both the blade surface length H and the blade tip angle α can be easily reduced with less number of flat surfaces. That is, it is possible to reduce the number of ridges formed by ridge lines where the flat surfaces meet. Therefore, an increase in puncture resistance due to ridges during puncture can be suppressed.

Furthermore, in the present embodiment, in the side view of the main body 2 (see FIGS. 1B and 2B), the line L extending along the third blade surface portion 7 intersects with the second blade surface portion 6 at a position not on the blade edge 9. With this configuration, the line L extending along the third blade surface portion 7 in the side view intersects with the second blade surface portion 6 at a position proximal of the blade edge 9. That is, as compared with the configuration in which the line extending along the third blade surface portion intersects with the blade edge in the side view, the acute inclination angle β with respect to the central axis O of the third blade surface portion 7 can be increased, and the blade surface length H can be decreased.

In the puncture needle 1 according to the present embodiment, a relation similar to the above relation is also established for the opposite side (not shown). Specifically, in the side view seen from the opposite side, the line L extending along the third blade surface portion 7 intersects with the first blade surface portion 5 at a position not on the blade edge 9. With this configuration, the line L extending along the third blade surface portion 7 intersects with the first blade surface portion 5 at a position proximal of the blade edge 9 in the side view seen from the opposite side.

Due to the configuration in which the side shown in FIGS. 1B and 2B and the opposite side have the similar configuration as described above, the blade surface length H can be reduced still further.

In the present embodiment, the main body 2 in the side view (see FIGS. 1B and 2B) is divided into two regions across the central axis O. The two regions are a distal region S1 including the needle tip 8 and a proximal region S2 not including the needle tip 8. In the present embodiment, at least a part of the third blade surface portion 7 is located in the proximal region S2 in the side view of the main body 2 (see FIGS. 1B and 2B).

Furthermore, in the present embodiment, in the side view of the main body 2 (see FIGS. 1B and 2B), the distal end of the third blade surface portion 7 reaches the central axis O. That is, the distal end of the third blade surface portion 7 in the present embodiment is located on the central axis O in the side view of the main body 2 (see FIGS. 1B and 2B). However, the third blade surface portion 7 may intersect with the central axis O in the side view of the main body 2 (see FIGS. 1B and 2B). That is, the third blade surface portion 7 extends across the distal region S1 and the proximal region S2 in the side view of the main body 2 (see FIGS. 1B and 2B), and the distal end of the third blade surface portion 7 may be located in the distal region S1 in the side view.

In the puncture needle 1 according to the present embodiment, a relation similar to the above relation is also established for the opposite side (not shown). Specifically, in the present embodiment, in the side view of the main body 2 seen from the opposite side (not shown), the distal end of the third blade surface portion 7 reaches the central axis O. That is, the distal end of the third blade surface portion 7 in the present embodiment is located on the central axis O in the side view of the main body 2 seen from the opposite side. However, the third blade surface portion 7 may intersect with the central axis O in the side view of the main body 2 seen from the opposite side. That is, the third blade surface portion 7 extends across the distal region S1 and the proximal region S2 in the side view of the main body 2 seen from the opposite side, and the distal end of the third blade surface portion 7 may be located in the distal region S1 in the side view.

Here, in the present embodiment, the distal end of the third blade surface portion 7 indicates a distal end of a ridge 14 formed by a ridge line where the third blade surface portion 7 meets both the first blade surface portion 5 and the second blade surface portion 6.

Further, in the present embodiment, the central axis O overlaps with the second blade surface portion 6 in the side view of the main body 2 (see FIGS. 1B and 2B). In other words, in the present embodiment, in the side view of the main body 2 (see FIGS. 1B and 2B), the central axis O intersects with the second blade surface portion 6. With this configuration, the length, in the central axis direction A, of the second blade surface portion 6 extending from the blade edge 9 can be relatively increased in the blade surface 4. If the proportion of the length of the second blade surface portion 6 in the central axis direction A in the blade surface length H can be increased, the blade tip angle α can be further reduced, whereby the puncture needle 1 with a thin blade tip can be easily achieved.

In the puncture needle 1 according to the present embodiment, a relation similar to the above relation is also established for the opposite side (not shown). Specifically, in the present embodiment, the central axis O overlaps with the first blade surface portion 5 in the side view of the main body 2 seen from the opposite side. In other words, in the present embodiment, the central axis O intersects with the first blade surface portion 5 in the side view of the main body 2 seen from the opposite side. With this configuration, the length, in the central axis direction A, of the first blade surface portion 5 extending from the blade edge 9 can be relatively increased in the blade surface 4.

Due to the configuration in which the side shown in FIGS. 1B and 2B and the opposite side have the similar configuration as described above, the blade tip angle α can be reduced still further, whereby the puncture needle 1 having a thin blade tip can be easily achieved.

Further, in the present embodiment, the first blade surface portion 5 and the second blade surface portion 6 extend to the proximal side beyond a midpoint M of the blade surface region T in the central axis direction A. With this configuration, the lengths, in the central axis direction A, of the first blade surface portion 5 and the second blade surface portion 6 that form the blade edge 9 can be relatively increased in the blade surface 4. When the lengths of the first blade surface portion 5 and the second blade surface portion 6 in the central axis direction A can be increased, the blade tip angle α can be relatively decreased, despite the first blade surface portion 5 and the second blade surface portion 6 being constituted by flat surfaces, respectively. Thus, the puncture needle 1 having a thin blade tip can be achieved.

Further, although both the first blade surface portion 5 and the second blade surface portion 6 extend to positions proximal of the midpoint M in the present embodiment, the configuration is not limited thereto. It is sufficient that at least one of the blade surface portion 5 and the second blade surface portion 6 extends to a position proximal of the midpoint M. However, when both the first blade surface portion 5 and the second blade surface portion 6 extend to positions proximal of the midpoint M as in the present embodiment, the blade tip angle α can be more easily reduced, compared to the configuration in which only one of the blade surface portion 5 or the second blade surface portion 6 extends to a position proximal of the midpoint M. Therefore, it is preferable that the first blade surface portion 5 and the second blade surface portion 6 are constituted by flat surfaces, and both the first blade surface portion 5 and the second blade surface portion 6 extend to positions proximal of the midpoint M, as in the present embodiment.

As the material of the main body 2 in the present embodiment, a metal material such as stainless steel, aluminum or an aluminum alloy, titanium or a titanium alloy, etc. can be used.

Hereinafter, further details of the puncture needle 1 according to the present embodiment will be described.

[Main Body 2]

The main body 2 in the present embodiment is a tubular body in which the inner diameter of the inner peripheral surface and the outer diameter of the outer peripheral surface are uniform in the central axis direction A, and the proximal end in the central axis direction A is connected to a medical device such as a syringe via a needle hub or the like. Therefore, the puncture needle 1 may have a needle hub or the like connected to the main body 2.

In the main body 2 in the present embodiment, the inner peripheral surface defines the hollow portion 10, and the inner diameter of the inner peripheral surface and the outer diameter of the outer peripheral surface are uniform in the central axis direction A. However, the configuration is not limited thereto. For example, the inner diameter of the inner peripheral surface and the outer diameter of the outer peripheral surface of the main body 2 may gradually decrease toward the distal side in the central axis direction A. Further, for example, the outer diameter of the main body 2 may be tapered so as to gradually decrease toward the distal side in the central axis direction A, and the inner diameter of the main body 2 may be uniform in the central axis direction A. Furthermore, the main body 2 may have, in a part thereof in the central axis direction A, a region where the inner diameter gradually decreases or gradually increases toward the distal side in the central axis direction A. That is, regarding the inner diameter and the outer diameter, the main body 2 may have various configurations according to a use or the like of the puncture needle 1.

[First Blade Surface Portion 5 and Second Blade Surface Portion 6]

As shown in FIG. 2A, proximal sides of each of the first blade surface portion 5 and the second blade surface portion 6 are contiguous with the third blade surface portion 7 in the central axis direction A.

Figure 3:
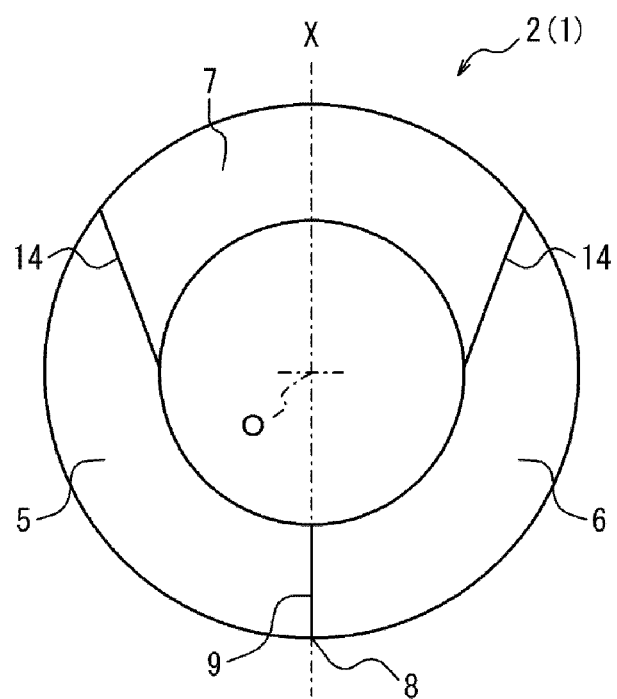
FIG. 3 is a view of the main body of the puncture needle shown in FIG. 1 as viewed from a distal side.

FIG. 3 is a view of the puncture needle 1 viewed from the distal side. FIGS. 4A, 4B, 4C, and 4D are sectional views taken along lines I-I, II-II, III-III, and IV-IV in FIG. 2A, respectively. The reference sign "X" shown in FIGS. 3 and 4 indicates a single virtual plane including the central axis O of the main body 2 and the needle tip 8, and is hereinafter referred to as "central plane X". The central plane X in the present embodiment is a plane including not only the needle tip 8 but also the blade edge 9, and the main body 2 in the present embodiment has a symmetrical structure with respect to the central plane X. In FIGS. 3 and 4, the ridge lines between the blade surface portions are indicated by solid lines.

Figure 4A:
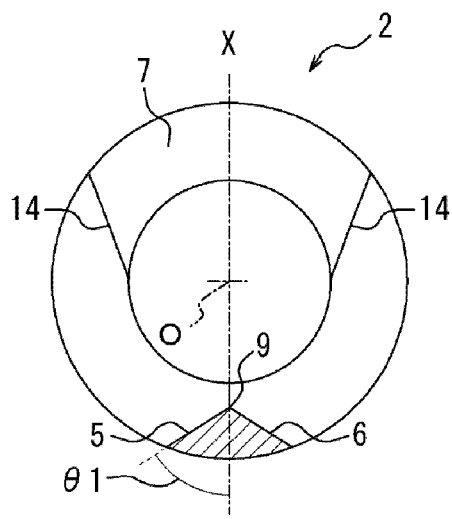
FIGS. 4A through 4D are sectional views taken along lines I-I, II-II, and IV-IV in FIG. 2A, respectively.

FIG. 4A shows a cross section along the line I-I in FIG. 2A, that is, a cross section perpendicular to the central axis direction A at a position where the blade edge 9 is formed in the central axis direction A. As shown in FIG. 4A, each of the first blade surface portion 5 and the second blade surface portion 6 extend so as to incline at an acute angle θ1 with respect to the central plane X.

Figure 4B:
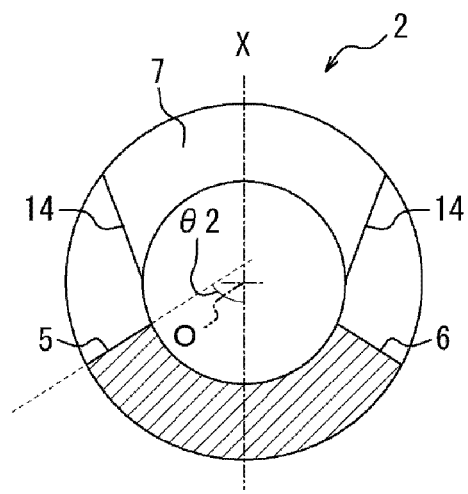

FIG. 4B shows a cross section along the line II-II in FIG. 2A, that is, a cross section that includes the first blade surface portion 5 and the second blade surface portion 6 but does not include the third blade surface portion 7, and which is perpendicular to the central axis direction A, at the position where the distal-end opening 11 is formed in the central axis direction A. As shown in FIG. 4B, an acute angle θ2 of each of the first blade surface portion 5 and the second blade surface portion 6 with respect to the central plane X in the cross section along the line II-II in FIG. 2A is equal to the angle θ1.

Figure 4C:
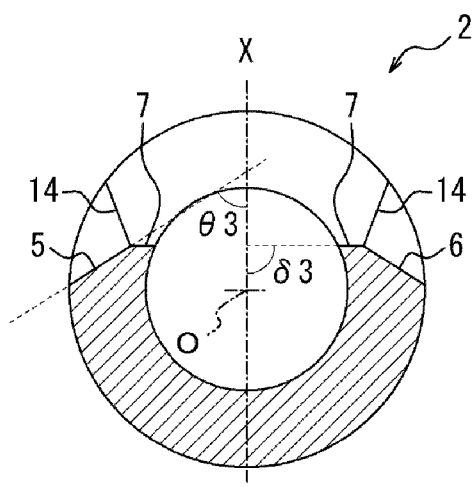

FIG. 4C shows a cross section along the line III-III in FIG. 2A, that is, a cross section that includes the first blade surface portion 5, the second blade surface portion 6, and the third blade surface portion 7, and that is perpendicular to the central axis direction A, at the position where the distal-end opening 11 is formed in the central axis direction A. As shown in FIG. 4C, an acute angle θ3 of each of the first blade surface portion 5 and the second blade surface portion 6 with respect to the central plane X in the cross section along the line III-III in FIG. 2A is equal to the angle θ1 and the angle θ2.

As described above, the acute angle θ of each of the first blade surface portion 5 and the second blade surface portion 6 with respect to the central plane X in a cross section perpendicular to the central axis direction A is constant regardless of the position in the central axis direction A.

[Third Blade Surface Portion 7]

The third blade surface portion 7 in the present embodiment is constituted by a flat surface. Specifically, the third blade surface portion 7 is a straight flat surface that is inclined so as to approach the central axis O with nearness to the needle tip 8 in the central axis direction A in the side view in FIG. 2B. The inclination angle β of the third blade surface portion 7 with respect to the central axis direction A is larger than the inclination angle of the outer peripheral surface of the main body 2 with respect to the central axis direction A in a cross section including the entire central axis O.

In the present embodiment, the outer diameter of the main body 2 of the puncture needle 1 is uniform in the central axis direction A, and when viewed in a cross section including the entire central axis O, the outer peripheral surface of the main body 2 extends in the central axis direction A. Therefore, if the third blade surface portion 7 is inclined with respect to the central axis direction A, the inclination angle β of the third blade surface portion 7 is larger than the inclination angle of the outer wall of the main body 2. However, when the main body of the puncture needle is configured such that the outer diameter gradually decreases or increases toward the distal side in the central axis direction A, the third blade surface portion is not only inclined with respect to the central axis direction A but also inclined with respect to the outer peripheral surface of the main body 2 in a cross section including the entire central axis O.

In the present embodiment, the proximal end of the inner edge of the blade surface 4 (see the point "N" in FIG. 2A) is provided on the inner edge of the third blade surface portion 7. Further, the inner edge of the blade surface 4 extends in a direction from the distal side towards the proximal side of the main body 2 from the distal end to the proximal end of the inner edge. More specifically, in the present embodiment, out of two points where the inner edge of the blade surface 4 intersects with the central plane X, the point on the distal side of the distal-end opening 11 is the distal end of the inner edge of the blade surface 4, and the point on the proximal side of the distal-end opening 11 is the proximal end of the inner edge of the blade surface 4 (see the point "N" in FIG. 2A). The inner edge of the blade surface 4 constantly extends in a direction from the distal side towards the proximal side of the main body 2 from the distal end to the proximal end of the inner edge of the blade surface 4, and there is no portion extending from the proximal side towards the distal side. The distal-end opening 11 has a teardrop shape when viewed from front (see FIG. 2A).

Next, the configuration of the third blade surface portion 7 in a cross section perpendicular to the central axis direction A will be described.

As shown in FIG. 4C, an angle δ3 of the third blade surface portion 7 with respect to the central plane X in the cross section along the line III-III in FIG. 2A is about 90 degrees. In other words, in the cross section along the line III-III in FIG. 2A, the third blade surface portion 7 extends linearly in a direction perpendicular to the central plane X.

Figure 4D:
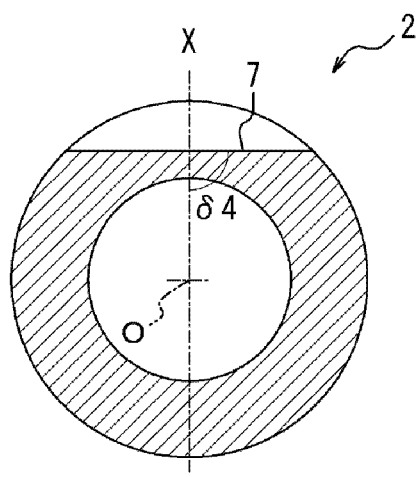

FIG. 4D shows a cross section along the line IV-IV in FIG. 2A, that is, a cross section that includes only the third blade surface portion 7, and that is perpendicular to the central axis direction A, at the position proximal to the distal-end opening 11 in the central axis direction A. As shown in FIG. 4D, an angle δ4 of the third blade surface portion 7 with respect to the central plane X in the cross section along the line IV-IV in FIG. 2A is about 90 degrees. In other words, in the cross section along the line IV-IV in FIG. 2A, the third blade surface portion 7 extends linearly in a direction perpendicular to the central plane X.

As described above, the angle δ of the third blade surface portion 7 with respect to the central plane X in the cross section perpendicular to the central axis direction A is constant at about 90 degrees regardless of the position in the central axis direction A (see FIGS. 4C and 4D).

[Shape of Blade Surface 4 in Side View]

The inclination angle β of the third blade surface portion 7 in the side view of the main body 2 (see FIG. 2B, etc.) is within a range of 13 degrees or more and 20 degrees or less. With this configuration, the blade tip angle α can be set to be substantially equal to or less than that of a so-called "regular bevel" (a puncture needle provided with a blade surface in which an inclination angle measured in the same manner as described above is 12 degrees) mainly used for intramuscular injection or the like, while setting the blade surface length H of the blade surface 4 to be shorter than the blade surface length of the "regular bevel" and to be substantially equal to the blade surface length of a so-called "short bevel" (a puncture needle provided with a blade surface in which an inclination angle measured in the same manner as described above is 18 degrees) mainly used for intravenous injection or the like.

That is, it is possible to achieve the puncture needle 1 that can reduce puncture resistance on the blade surface 4 and can be easily and reliably inserted into a vessel, with a short blade surface length by which the puncture needle 1 is unlikely to pierce through a vessel such as a vein. Further, since the puncture resistance in the vicinity of the needle tip 8 can be reduced, an amount of change in the puncture resistance can be reduced, and an amount of change in force applied by a medical worker in the puncture direction during puncture can also be reduced. Therefore, it is possible to achieve the puncture needle 1 that is easily operated by a medical worker when puncturing.

Further, although the third blade surface portion 7 in the present embodiment is constituted by a single flat surface extending to the proximal end of the blade surface 4, another blade surface portion may be provided on the side proximal to the third blade surface portion 7. For example, a blade surface portion that is contiguous with the third blade surface portion 7 and has an inclination angle smaller than the inclination angle β may be provided. With this configuration, the puncture resistance at the proximal end portion of the blade surface 4 during puncture can be reduced. Alternatively, another blade surface portion that is contiguous with the third blade surface portion 7 and that is constituted by a convex curved surface may be provided. The puncture resistance at the proximal end portion of the blade surface 4 during puncture can be similarly reduced.

Notably, it is preferable to set the blade tip angle α to 15 degrees to 27 degrees, while keeping an angle of the line L with respect to the central axis O shown in FIG. 2B within the range of 13 degrees or more and 20 degrees or less. If the blade tip angle α is less than 15 degrees, the blade tip becomes too thin, so that predetermined performance may not be able to be satisfied due to damage or the like during a manufacturing process. Thus, the manufacture of such a blade tip is difficult. On the other hand, if the angle exceeds 27 degrees, the blade tip angle becomes equal to the blade tip angle α of the so-called short bevel, so that the puncture resistance during puncture increases.

Second Embodiment

Next, a puncture needle 101 as another embodiment different from the above-described puncture needle 1 according to the first embodiment will be described. The puncture needle 101 according to the present embodiment is different from the puncture needle 1 described above in the configuration of the blade surface, and is similar to the puncture needle 1 in other configurations.

Figure 5A:
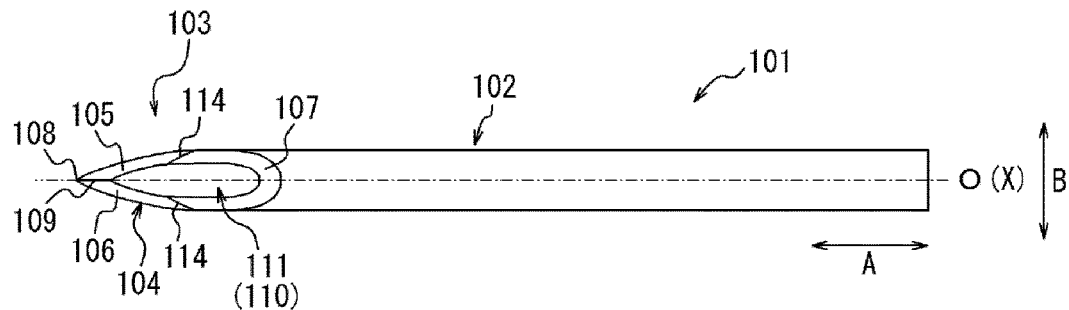
FIGS. 5A through 5D are a front view, a side view, a rear view, and a perspective view of a main body of a puncture needle as one embodiment, respectively.
Figure 5B:
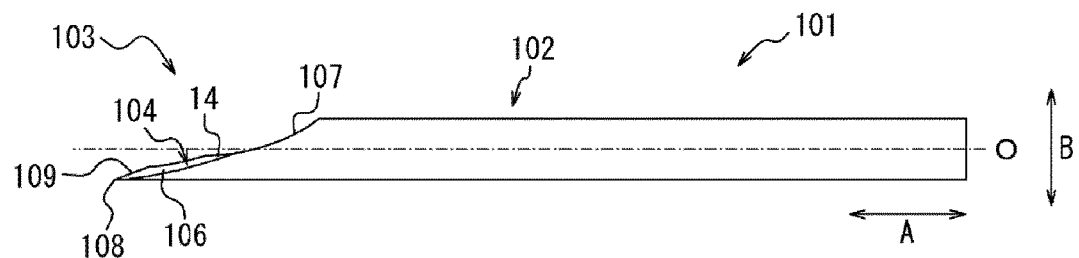
Figure 5C:
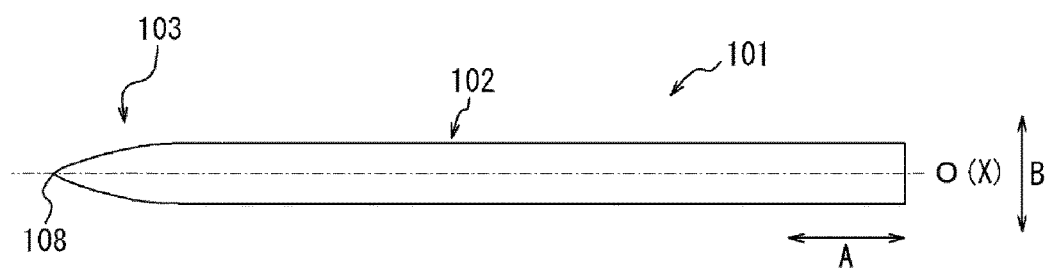
Figure 5D:
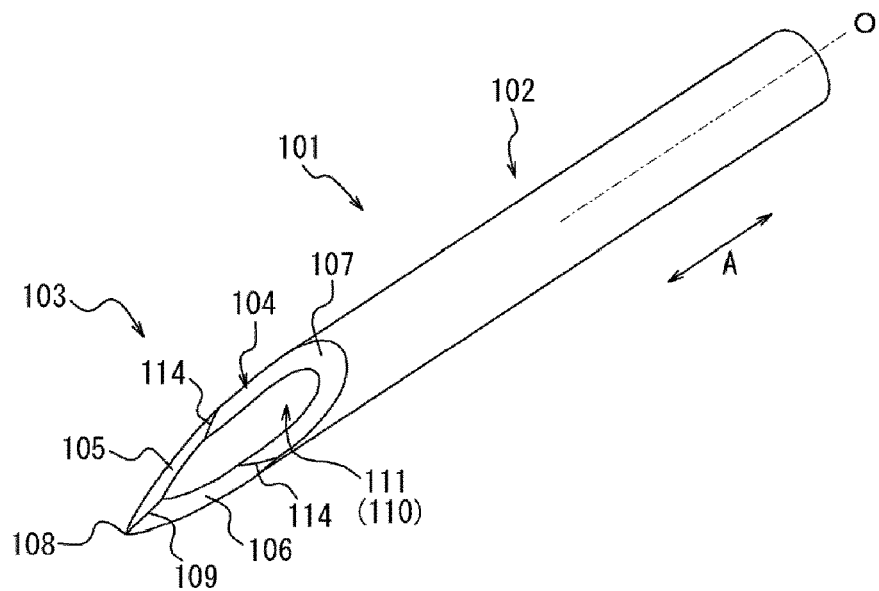
Figure 6A:
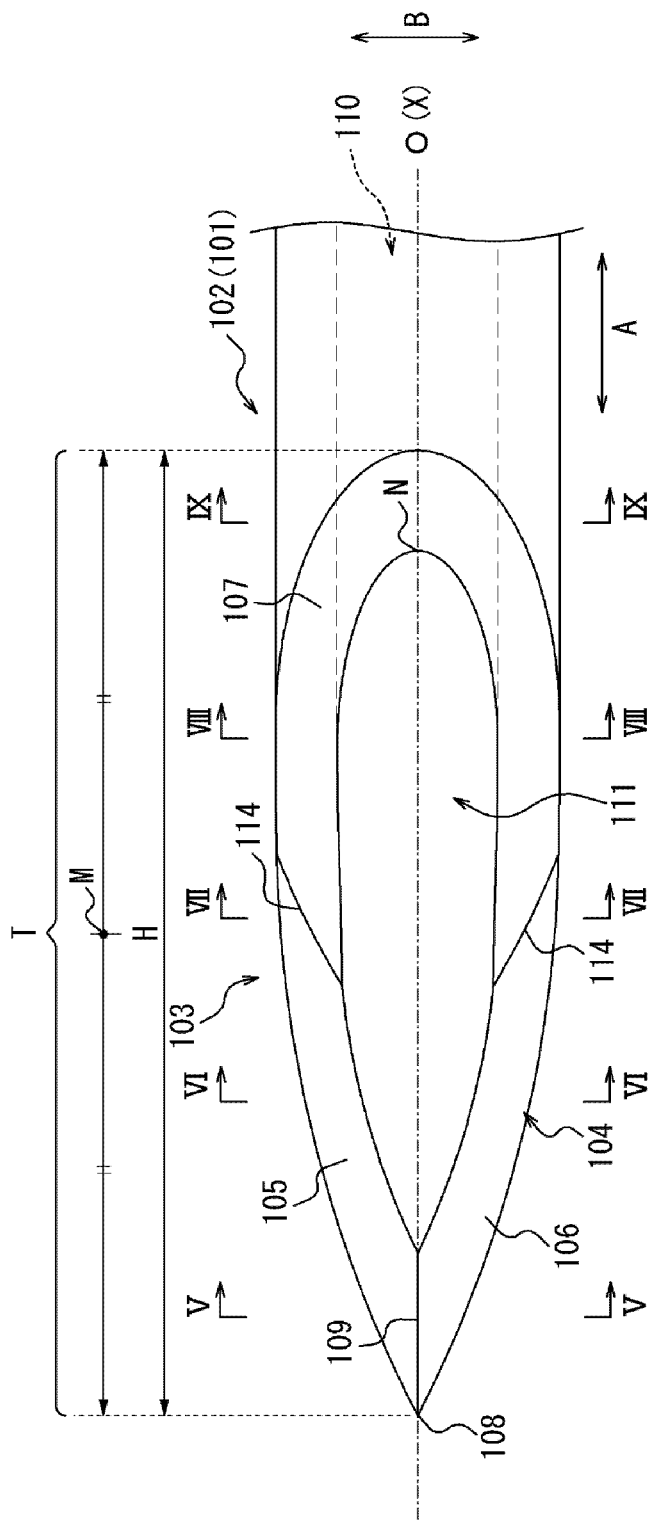
FIGS. 6A and 6B are enlarged views showing the vicinity of a distal end portion of the main body of the puncture needle shown in FIGS. 5A and 5B, respectively.
Figure 6B:
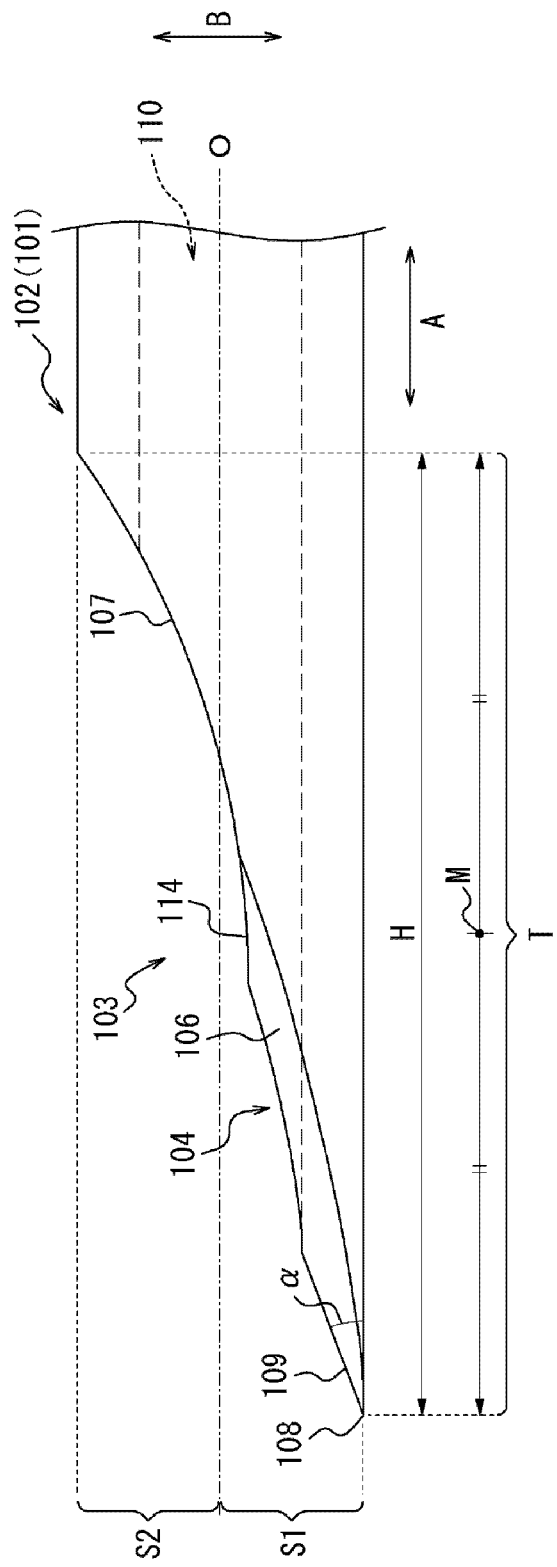

FIG. 5 is a view showing a main body 102 of the puncture needle 101 as one embodiment. Specifically, FIG. 5A is a front view of the main body 102 of the puncture needle 101, FIG. 5B is a side view of the main body 102 of the puncture needle 101, and FIG. 5C is a rear view of the main body 102 of the puncture needle 101. FIG. 5D is a perspective view of the main body 102 of the puncture needle 101. Further, FIG. 6A is an enlarged front view of a part of the main body 102 of the puncture needle 101 shown in FIG. 5A. FIG. 6B is an enlarged side view of a part of the main body 102 of the puncture needle 101 shown in FIG. 5B.

As shown in FIGS. 5 and 6, a blade surface 104 is formed on a distal end portion 103 of a rod-shaped main body 102 of the puncture needle 101. The blade surface 104 includes a first blade surface portion 105, a second blade surface portion 106, and a third blade surface portion 107.

The first blade surface portion 105 and the second blade surface portion 106 form a blade edge 109 having a needle tip 108 as one end by a ridge line where they meet. The main body 102 has a hollow portion 110 having a distal-end opening 111 formed on one end. The first blade surface portion 105 and the second blade surface portion 106 of the puncture needle 101 is different from the first blade surface portion 5 and the second blade surface portion 6 of the puncture needle 1 in length in the central axis direction A, and are the same in other configurations. For example, in the present embodiment, the first blade surface portion 105 and the second blade surface portion 106 also extend to the proximal side beyond a midpoint M of a blade surface region T in the central axis direction A of the main body 102.

A proximal side of the first blade surface portion 105 is contiguous with the third blade surface portion 107. Further, a proximal side of the second blade surface portion 106 is contiguous with the third blade surface portion 107. That is, the third blade surface portion 107 in the present embodiment is contiguous with proximal sides of both the first blade surface portion 105 and the second blade surface portion 106.

In a side view of the main body 102 (see FIGS. 5B and 6B), the third blade surface portion 107 has a concave shape. More specifically, the third blade surface portion 107 in the present embodiment is constituted by a concave curved surface. Hereinafter, the side view of the main body 102 shown in FIGS. 5B and 6B is referred to as a "side view of the main body 102".

With the configuration described above, it becomes easier to achieve a thinner blade tip as compared with the existing puncture needle 501 shown in FIG. 11. That is, the puncture needle 101 having a small blade tip angle α is easily achieved. Therefore, as compared with the existing puncture needle 501 shown in FIG. 11, a configuration in which both the blade surface length H and the blade tip angle α are reduced is easily achieved.

Further, the third blade surface portion 107 in the present embodiment constitutes the proximal end of the blade surface 104. In other words, a proximal side of the third blade surface portion 107 in the present embodiment is contiguous with a distal side of the cylindrical outer peripheral surface of the main body 102. Therefore, in the present embodiment, a distal side of the third blade surface portion 107 is contiguous with the proximal sides of the first blade surface portion 105 and the second blade surface portion 106 as described above, and a proximal side of the third blade surface portion 107 is contiguous with the distal side of the cylindrical outer peripheral surface of the main body 102.

As described above, the blade surface 104 in the present embodiment is formed by continuously connecting the third blade surface portion 107 constituted by a concave curved surface to both the first blade surface portion 105 and the second blade surface portion 106 each constituted by a single flat surface.

The inner edge of the blade surface 104 in the present embodiment is constituted by the inner edge of the first blade surface portion 105, the inner edge of the second blade surface portion 106, and the inner edge of the third blade surface portion 107. The inner edge of the blade surface 104 defines the distal-end opening 111, which is one end of the hollow portion 110 of the main body 102 on the distal side of the main body 102.

The outer edge of the blade surface 104 in the present embodiment is constituted by the outer edge of the first blade surface portion 105, the outer edge of the second blade surface portion 106, and the outer edge of the third blade surface portion 107. The outer edge of the blade surface 104 defines a blade surface region T where the blade surface 104 is formed.

In the present embodiment, the main body 102 in the side view (see FIGS. 5B and 6B) is divided into two regions across the central axis O. The two regions are a distal region S1 including the needle tip 108 and a proximal region S2 not including the needle tip 108. In the present embodiment, at least a part of the third blade surface portion 107 is located in the proximal region S2 in the side view of the main body 102 (see FIGS. 5B and 6B).

Furthermore, in the present embodiment, in the side view of the main body 102 (see FIGS. 5B and 6B), the distal end of the third blade surface portion 107 reaches the central axis O. More specifically, in the present embodiment, in the side view of the main body 102 (see FIGS. 5B and 6B), the third blade surface portion 107 intersects with the central axis O. That is, the third blade surface portion 107 in the present embodiment extends across the distal region S1 and the proximal region S2 in the side view of the main body 102 (see FIGS. 5B and 6B), and the distal end of the third blade surface portion 107 is located in the distal region S1 in the side view.

In the puncture needle 101 in the present embodiment, a relation similar to the abovementioned relation is also established for the side (hereinafter referred to as the "opposite side") opposite to the side shown in FIGS. 5B and 6B. Specifically, in the present embodiment, in the side view of the main body 102 seen from the opposite side (not shown), the distal end of the third blade surface portion 107 reaches the central axis O. More specifically, in the present embodiment, the third blade surface portion 107 intersects with the central axis O in the side view of the main body 102 seen from the opposite side. That is, the third blade surface portion 107 in the present embodiment extends across the distal region S1 and the proximal region S2 in the side view of the main body 102 seen from the opposite side, and the distal end of the third blade surface portion 107 is located in the distal region S1 in this side view.

Here, in the present embodiment, the distal end of the third blade surface portion 107 indicates a distal end of a ridge 114 formed by a ridge line where the third blade surface portion 107 meets both the first blade surface portion 105 and the second blade surface portion 106.

Further, although the central axis O does not overlap with the second blade surface portion 106 in the side view of the main body 102 (see FIGS. 5B and 6B) in the present embodiment, the central axis O may overlap with the second blade surface portion 106 as in the first embodiment. That is, the central axis O may intersect with the second blade surface portion 106 in the side view of the main body 102 (see FIGS. 5B and 6B). With this configuration, the length, in the central axis direction A, of the second blade surface portion 106 extending from the blade edge 109 can be relatively increased in the blade surface 104. If the proportion of the length of the second blade surface portion 106 in the central axis direction A in the blade surface length H can be increased, the blade tip angle α can be further reduced, whereby the puncture needle 101 with a thin blade tip can be easily achieved.

In the puncture needle 101 according to the present embodiment, a relation similar to the above relation is also established for the opposite side (not shown). Specifically, in the present embodiment, the central axis O does not overlap with the first blade surface portion 105 in the side view of the main body 102 seen from the opposite side. However, the central axis O may intersect with the first blade surface portion 105 also in the side view of the main body 102 seen from the opposite side. With this configuration, the length, in the central axis direction A, of the first blade surface portion 105 extending from the blade edge 109 can be relatively increased in the blade surface 104.

Due to the configuration described above in which the central axis O intersects with the second blade surface portion 106 or the first blade surface portion 105 in both the side view shown in FIGS. 5B and 6B and the side view seen from the opposite side, the blade tip angle α can be reduced still further, whereby the puncture needle 101 having a thin blade tip can be easily achieved.

In addition, the inclination angle β of the third blade surface portion 107 in the side view of the main body 102 (see FIG. 5B, etc.) is within a range of 13 degrees or more and 20 degrees or less. With this configuration, the blade tip angle α can be set to be substantially equal to or less than that of the abovementioned "regular bevel" mainly used for intramuscular injection or the like, while setting the blade surface length H of the blade surface 104 to be shorter than the blade surface length of the "regular bevel" and to be substantially equal to the blade surface length of the abovementioned "short bevel" mainly used for intravenous injection or the like.

That is, it is possible to achieve the puncture needle 101 that can reduce puncture resistance on the blade surface 104 and can be easily and reliably inserted into a vessel, with a short blade surface length by which the puncture needle 101 is unlikely to penetrate a vessel such as a vein. Further, since the puncture resistance in the vicinity of the needle tip 108 can be reduced, an amount of change in the puncture resistance can be reduced, and an amount of change in force applied by a medical worker in the puncture direction during puncture can also be reduced. Therefore, it is possible to achieve the puncture needle 101 that is easily operated by a medical worker when puncturing.

Next, the configuration of the blade surface 104 in a cross section perpendicular to the central axis direction A will be described.

Figure 7:
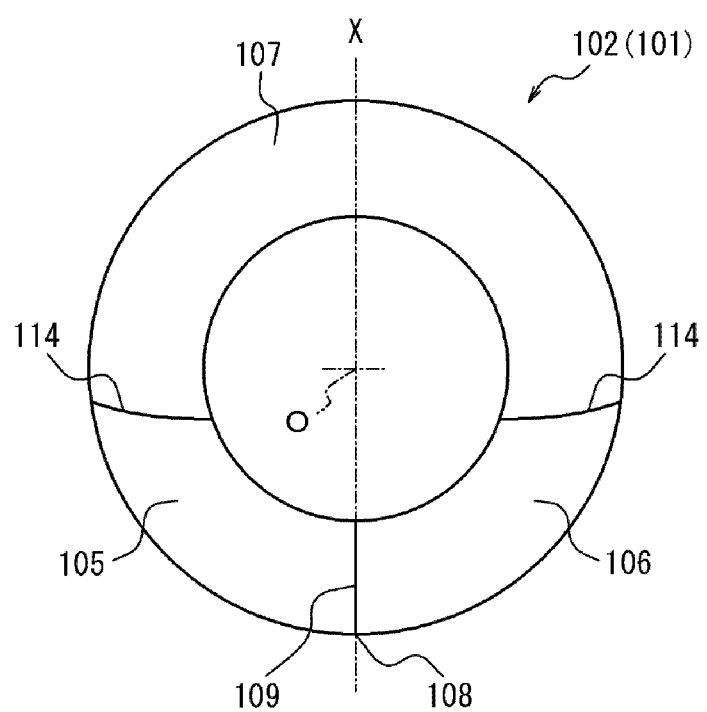
FIG. 7 is a view of the main body of the puncture needle shown in FIG. 5 as viewed from a distal side.

FIG. 7 is a view of the puncture needle 101 viewed from the distal side. FIGS. 8A, 8B, 8C, 8D, and 8E are sectional views along lines V-V, VI-VI, VII-VII, VIII-VIII, and IX-IX in FIG. 6A, respectively. The main body 102 in the present embodiment has a symmetrical structure with respect to the central plane X. In FIGS. 7 and 8, ridge lines between the blade surface portions are indicated by solid lines.

Figure 8A:
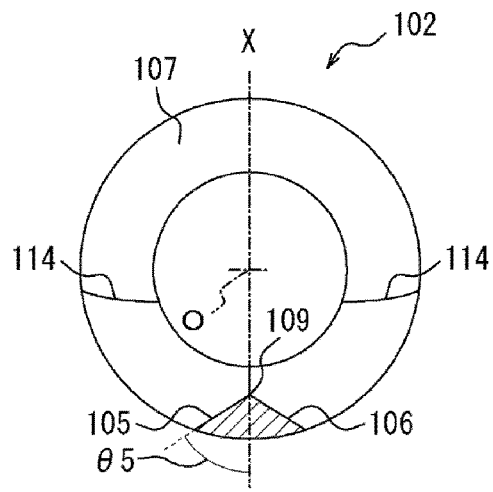
FIGS. 8A through 8E are sectional views taken along lines V-V, VI-VI, VII-VII, VIII-VIII, and IX-IX in FIG. 6A, respectively.

FIG. 8A shows a cross section along the line V-V in FIG. 6A, that is, a cross section perpendicular to the central axis direction A at a position where the blade edge 109 is formed in the central axis direction A. As shown in FIG. 8A, each of the first blade surface portion 105 and the second blade surface portion 106 extend so as to incline at an acute angle θ5 with respect to the central plane X.

Figure 8B:
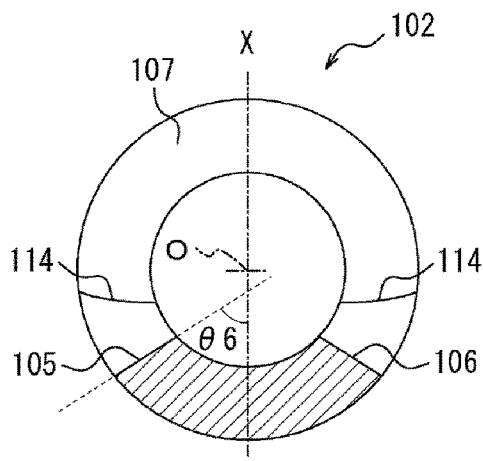

FIG. 8B shows a cross section along the line VI-VI in FIG. 6A, that is, a cross section that includes the first blade surface portion 105 and the second blade surface portion 106 but does not include the third blade surface portion 107, and that is perpendicular to the central axis direction A, at the position where the distal-end opening 111 is formed in the central axis direction A. As shown in FIG. 8B, an acute angle θ6 of each of the first blade surface portion 105 and the second blade surface portion 106 with respect to the central plane X in the cross section along the line VI-VI in FIG. 6A is equal to the angle θ5.

Figure 8C:
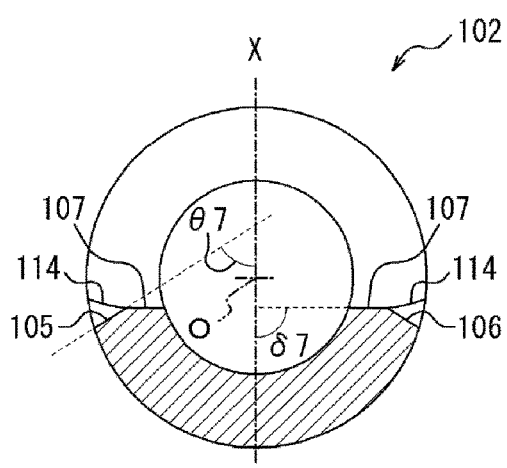

FIG. 8C shows a cross section along the line VII-VII in FIG. 6A, that is, a cross section that includes the first blade surface portion 105, the second blade surface portion 106, and the third blade surface portion 107, and that is perpendicular to the central axis direction A, at the position where the distal-end opening 111 is formed in the central axis direction A. As shown in FIG. 8C, an acute angle θ7 of each of the first blade surface portion 105 and the second blade surface portion 106 with respect to the central plane X in the cross section along the line VII-VII in FIG. 6A is equal to the angle θ5 and the angle θ6.

As described above, the acute angle θ of each of the first blade surface portion 105 and the second blade surface portion 106 with respect to the central plane X in the cross section perpendicular to the central axis direction A is constant regardless of the position in the central axis direction A.

Further, as shown in FIG. 8C, an angle δ7 of the third blade surface portion 107 with respect to the central plane X in the cross section along the line VII-VII in FIG. 6A is about 90 degrees. In other words, in the cross section along the line VII-VII in FIG. 6A, the third blade surface portion 107 extends linearly in a direction perpendicular to the central plane X.

Figure 8D:
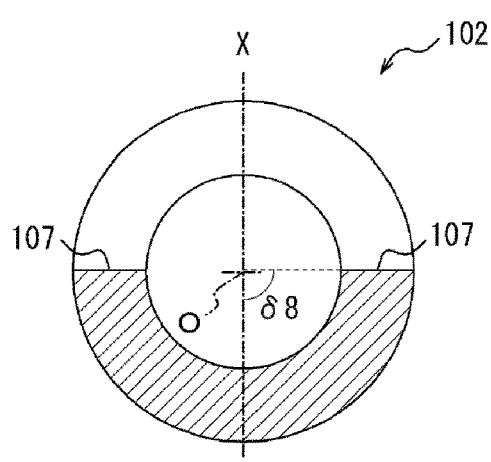

FIG. 8D shows a cross section along the line VIII-VIII in FIG. 6A, that is, a cross section that includes only the third blade surface portion 107, and that is perpendicular to the central axis direction A, at the position where the distal-end opening 111 is formed in the central axis direction A. As shown in FIG. 8D, an angle δ8 of the third blade surface portion 107 with respect to the central plane X in the cross section along the line VIII-VIII in FIG. 6A is about 90 degrees. In other words, in the cross section along the line VIII-VIII in FIG. 6A, the third blade surface portion 107 extends linearly in a direction perpendicular to the central plane X.

Figure 8E:
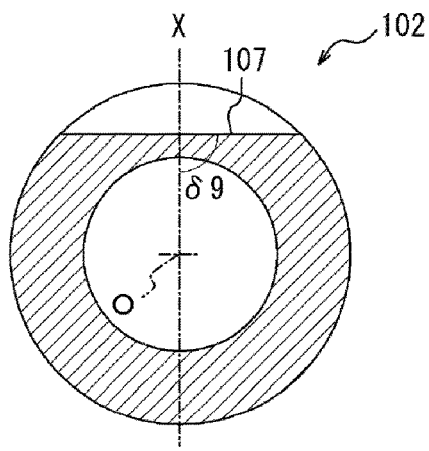
Figure 9A:
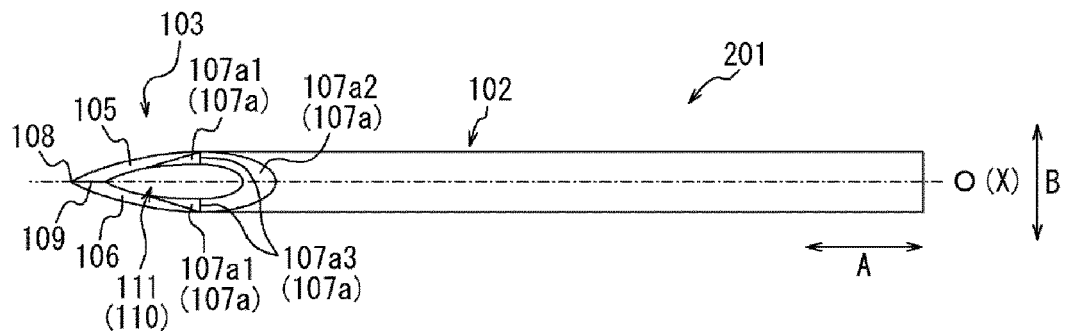
FIGS. 9A through 9D are a front view, a side view, a rear view, and a perspective view of a modification of the main body of the puncture needle shown in FIG. 7, respectively.
Figure 9B:
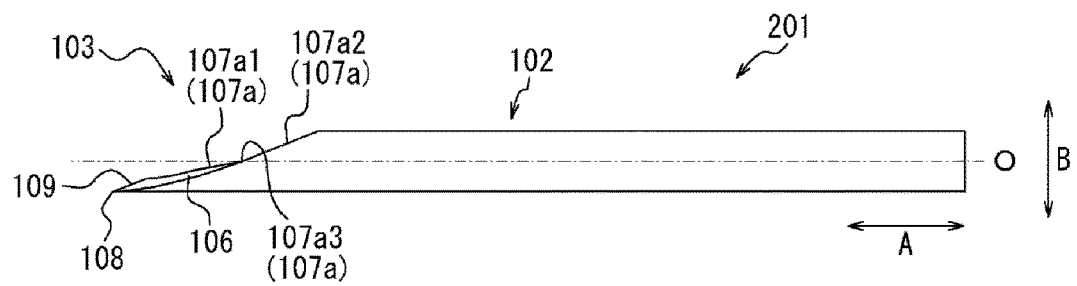
Figure 9C:
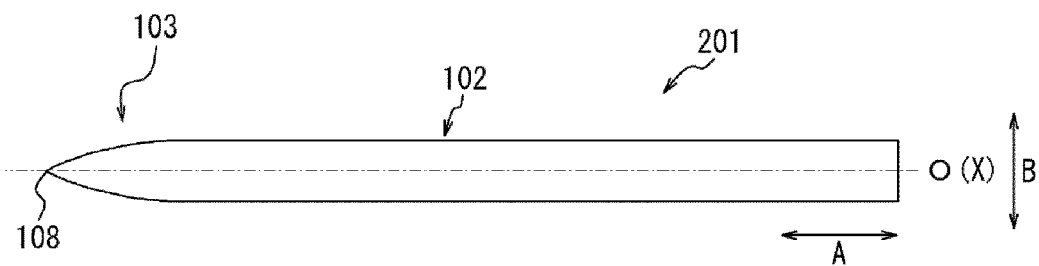
Figure 9D:
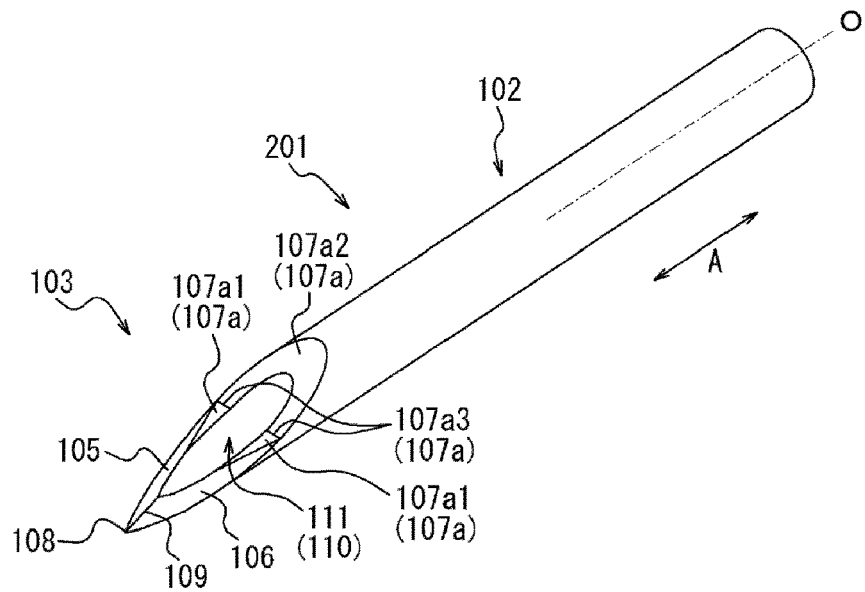

FIG. 8E shows a cross section along the line IX-IX in FIG. 6A, that is, a cross section that includes only the third blade surface portion 107, and that is perpendicular to the central axis direction A, at the position proximal to the distal-end opening 111 in the central axis direction A. As shown in FIG. 8E, an angle δ9 of the third blade surface portion 107 with respect to the central plane X in the cross section along the line IX-IX in FIG. 6A is about 90 degrees. In other words, in the cross section along the line IX-IX in FIG. 6A, the third blade surface portion 107 extends linearly in a direction perpendicular to the central plane X.

As described above, the angle δ of the third blade surface portion 107 with respect to the central plane X in the cross section perpendicular to the central axis direction A is constant at about 90 degrees regardless of the position in the central axis direction A (see FIGS. 8C, 8D, and 8E).

The third blade surface portion 107 in the present embodiment is constituted by a concave curved surface contiguous with proximal sides of both the first blade surface portion 105 and the second blade surface portion 106. However, it is not limited to have the above configuration. A puncture needle 201 may be used that includes a third blade surface portion 107a constituted by a flat surface that is formed into a concave shape by a plurality of flat surfaces (e.g., three flat surfaces) as shown in FIGS. 9 and 10.

Figure 10A:
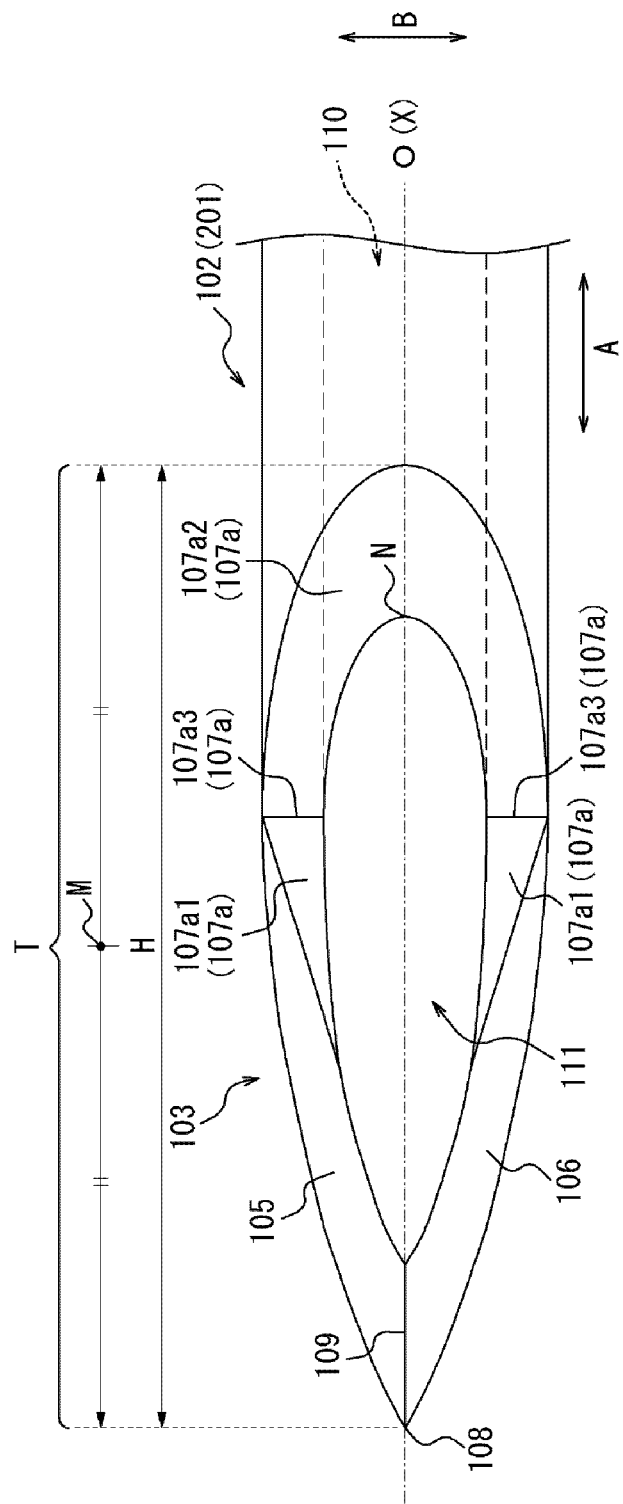
FIGS. 10A and 10B are enlarged views showing the vicinity of a distal end portion of the main body of the puncture needle shown in FIGS. 9A and 9B, respectively.
Figure 10B:
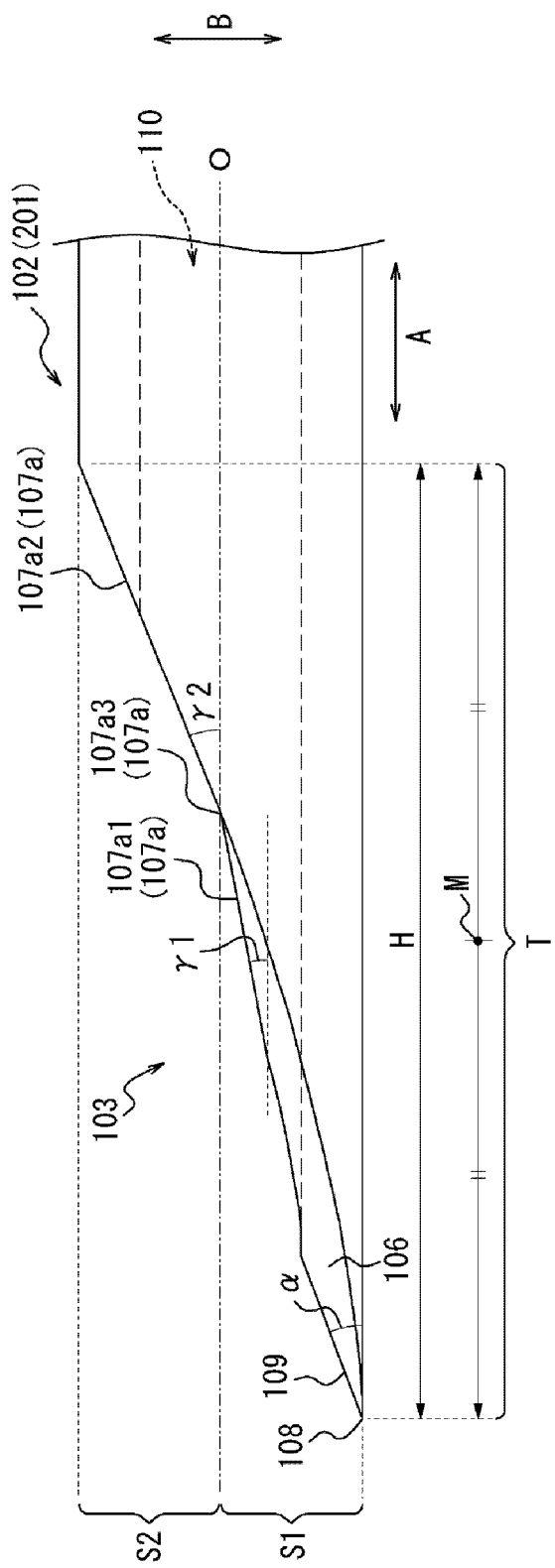

The third blade surface portion 107a shown in FIGS. 9 and 10 includes two distal-side flat portions 107a1 and one proximal-side flat portion 107a2. One of the distal-side flat portions 107a1 is constituted by a single flat surface, and is contiguous with the first blade surface portion 105 on the proximal side of the first blade surface portion 105. The other distal-side flat portion 107a1 is constituted by a single flat surface, and is contiguous with the second blade surface portion 106 on the proximal side of the second blade surface portion 106. The proximal-side flat portion 107a2 is constituted by a single flat surface. Further, the proximal-side flat portion 107a2 is contiguous with the one distal-side flat portion 107a1 on the proximal side of the one distal-side flat portion 107a1, and a concave bottom 107a3 is formed by a ridge line where the proximal-side flat portion 107a2 meets the one distal-side flat portion 107a1. Moreover, the proximal-side flat portion 107a2 is contiguous with the other distal-side flat portion 107a1 on the proximal side of the other distal-side flat portion 107a1, and a concave bottom 107a3 is formed by a ridge line where the proximal-side flat portion 107a2 meets the other distal-side flat portion 107a1. The two distal-side flat portions 107a1 are included in the same virtual plane. Therefore, in the side view of the main body 102 (see FIGS. 9B and 10B), acute inclination angles γ1 of the two distal-side flat portions 107a1 with respect to the central axis O are equal to each other. The third blade surface portion 107a has a concave shape in the side view of the main body 102 (see FIGS. 9B and 10B). That is, in the side view described above, the inclination angles γ1 of the two distal-side flat portions 107a1 with respect to the central axis O are smaller than the acute inclination angle γ2 of the proximal-side flat portion 107a2 with respect to the central axis O.

Further, the third blade surface portion is not limited to the third blade portion 107a shown in FIGS. 9 and 10. A third blade surface portion having both a flat surface and a curved surface may be used. As described above, the configuration of the third blade surface portion is not particularly limited, as long as the third blade surface portion forms a concave shape in a side view. However, when the third blade surface portion 107 constituted by one concave curved surface shown in FIGS. 5 and 6, or the third blade surface portion 107a constituted by a plurality of flat surfaces shown in FIGS. 9 and 10 is used, the third blade surface portion having a concave shape in a side view (see FIGS. 5B, 6B, 9B, and 10B) can be achieved with a simple configuration.

Lastly, a method for manufacturing the puncture needle 1 described above will be described. First, a first original-form blade surface portion and a second original-form blade surface portion that are the original forms of the first blade surface portion 5 and the second blade surface portion 6 are formed in a tubular member having, on a distal end portion thereof, an inclined surface inclined with respect to the central axis. Next, the proximal ends of the first original-form blade surface portion and the second original-form blade surface portion are machined by cutting, grinding, electro-discharge (including wire electric discharge), or the like to form the first blade surface portion 5, the second blade surface portion 6, and the third blade surface portion 7. With this process, the blade surface 4 of the puncture needle 1 can be formed. Note that the processing order of the blade surface 4 of the puncture needle 1 is not limited to the above order. For example, after formation of a third original-form blade surface portion, which is the original form of the third blade surface portion 7, the first blade surface portion 5, the second blade surface portion 6, and the third blade surface portion 7 may be respectively formed.

While the method for forming the blade surface 4 of the puncture needle 1 has been described above, the similar method can be used for forming the blade surface of the puncture needle 101 shown in FIGS. 5 to 8 and the blade surface of the puncture needle 201 shown in FIGS. 9 and 10.

The puncture needle according to the present disclosure is not limited to have the specific configuration indicated in the above embodiments, and various modifications and changes are possible without departing from the scope of the claims.

INDUSTRIAL APPLICABILITY

The present disclosure relates to a puncture needle.

REFERENCE SIGNS LIST 1, 101, 201 Puncture needle
2, 102 Main body
3, 103 Distal end portion
4, 104 Blade surface
5, 105 First blade surface portion
6, 106 Second blade surface portion
7, 107, 107a Third blade surface portion
8, 108 Needle tip
9, 109 Blade edge
10, 110 Hollow portion
11, 111 Distal-end opening
14, 114 Ridge
107a1 Distal-side flat portion
107a2 Proximal-side flat portion
107a3 Concave bottom
501 Puncture needle
502 Main body
504 Blade surface
506 First blade surface portion
507 Second blade surface portion A Central axis direction of main body
B Direction perpendicular to central axis direction of main body
H Blade surface length
L, L' Line extending along third blade surface portion in side view of main body
M Midpoint of blade surface region
N Proximal end of inner edge of blade surface
O Central axis of main body
S1 Distal region
S2 Proximal region
T Blade surface region
X Central plane
α, α' Blade tip angle
β, γ1, γ2, β' Inclination angle
θ, δ Angle between blade surface portion and central plane in cross section perpendicular to central axis direction

The invention claimed is:

1. A puncture needle comprising:
a rod-shaped main body; and
a blade surface located at a distal end portion of the main body, wherein the blade surface comprises:
a first blade surface portion,
a second blade surface portion, and
a third blade surface portion,
wherein the first blade surface portion and the second blade surface portion form a blade edge at a first ridge where the first blade surface portion and the second blade surface portion meet, and a needle tip is formed at an end of the blade edge,
wherein the third blade surface portion is contiguous with a proximal side of at least the first blade surface portion at a second ridge, and the third blade surface portion is a single flat surface that is inclined with respect to a central axis of the main body,
wherein, in a first side view of the main body in which the first blade surface portion is visible and the single flat surface of the third blade surface portion appears straight, a line extending along the third blade surface portion through a proximal end and a distal end of the third blade surface portion intersects with the first blade surface portion at a position not on the second ridge,
wherein, in the first side view, the proximal end of the third blade surface portion is contiguous with a cylindrical outer peripheral surface of the main body, and the distal end of the third blade surface portion is a distal-most point of the third blade surface portion that appears straight, and
wherein the first blade surface portion and the second blade surface portion extend to a proximal side of a midpoint of the blade surface in a central axis direction of the main body.

2. The puncture needle according to claim 1, wherein, in the first side view, the line extending along the third blade surface portion intersects with the first blade surface portion at a position not on the blade edge.

3. The puncture needle according to claim 1, wherein, in the first side view, the distal end of the third blade surface portion reaches the central axis, or the third blade surface portion intersects with the central axis.

4. The puncture needle according to claim 1, wherein, in the first side view, the central axis overlaps with the first blade surface portion.

5. The puncture needle according to claim 1, wherein the third blade surface portion is contiguous with a proximal side of the second blade surface portion.

6. The puncture needle according to claim 1, wherein, in a second side view of the main body in which the second blade surface portion is visible and the single flat surface of the third blade surface portion appears straight, a line extending along the third blade surface portion intersects with the second blade surface portion.

7. A puncture needle comprising:
   a rod-shaped main body; and
   a blade surface located at a distal end portion of the main body, wherein the blade surface comprises:
      a first blade surface portion,
      a second blade surface portion, and
      a third blade surface portion,
   wherein the first blade surface portion and the second blade surface portion form a blade edge at a first ridge where the first blade surface portion and the second blade surface portion meet, and a needle tip is formed at an end of the blade edge,
   wherein the third blade surface portion is contiguous with a proximal side of the first blade surface portion at a second ridge and a proximal side of the second blade surface portion at a third ridge, and the third blade surface portion is a single flat surface that is inclined with respect to a central axis of the main body, and
   wherein, in a first side view of the main body in which the first blade surface portion is visible and the single flat surface of the third blade surface portion appears straight, a line extending along the third blade surface portion intersects with the first blade surface portion at a position not on the second ridge,
   wherein, in a second side view of the main body in which the second blade surface portion is visible and the single flat surface appears straight, a line extending along the third blade surface portion through a proximal end and a distal end of the third blade surface portion intersects with the second blade surface portion at a position not on the third ridge,
   wherein, in the first side view, the proximal end of the third blade surface portion is contiguous with a cylindrical outer peripheral surface of the main body, and the distal end of the third blade surface portion is a distal-most point of the third blade surface portion that appears straight, and
   wherein the first blade surface portion and the second blade surface portion extend to a proximal side of a midpoint of the blade surface in a central axis direction of the main body.

8. The puncture needle according to claim 7, wherein:
   in the first side view, the line extending along the third blade surface portion intersects with the first blade surface portion at a position not on the blade edge, and
   in the second side view, the line extending along the third blade surface portion intersects with the second blade surface portion at a position not on the blade edge.

9. The puncture needle according to claim 7, wherein, in the first and second side views, the distal end of the third blade surface portion reaches the central axis, or the third blade surface portion intersects with the central axis.

10. The puncture needle according to claim 7, wherein, in the first and second side views, the central axis overlaps with the first blade surface portion and the second blade surface portion.

* * * * *